United States Patent [19]

Zuk et al.

[11] Patent Number: 4,956,275

[45] Date of Patent: Sep. 11, 1990

[54] MIGRATORY DETECTION IMMUNOASSAY

[75] Inventors: Robert F. Zuk, Burlingame; Richard D. Armenta, Sunnyvale; Jonathan Briggs, Los Altos Hills, all of Calif.

[73] Assignee: Molecular Devices Corporation, Palo Alto, Calif.

[21] Appl. No.: 38,294

[22] Filed: Apr. 14, 1987

[51] Int. Cl.[5] .............. G01N 33/535; G01N 33/558; G01N 33/543; C12M 1/40

[52] U.S. Cl. .............................. 435/7; 435/288; 435/291; 435/805; 435/25; 436/514; 436/518; 436/807; 436/810

[58] Field of Search ............ 436/514, 515, 518, 807, 436/810; 435/7, 288, 291, 805, 25

[56] References Cited

U.S. PATENT DOCUMENTS

| 4,235,601 | 11/1980 | Deutsch et al. | |
| 4,435,504 | 3/1984 | Zuk et al. | 435/7 |
| 4,446,232 | 5/1984 | Liotta | 435/7 |
| 4,533,629 | 8/1985 | Litman et al. | 435/7 |
| 4,613,567 | 9/1986 | Yasoshima et al. | 435/7 |
| 4,668,619 | 5/1987 | Greenquist et al. | 435/7 |
| 4,690,907 | 9/1987 | Hibino et al. | 436/514 |
| 4,746,631 | 5/1988 | Clagett | 436/518 |
| 4,774,174 | 9/1988 | Giegel et al. | 435/5 |

FOREIGN PATENT DOCUMENTS 3445816 6/1986 Australia ...................... 435/805

Primary Examiner—Esther M. Kepplinger
Assistant Examiner—Toni R. Scheiner
Attorney, Agent, or Firm—Allegretti & Witcoff, Ltd.

[57] ABSTRACT

Novel methods and devices are provided for detecting analytes, where the sample is placed upstream from a reagent which is a component of a signal-producing system. The detection zone is provided upstream from the sample, where the amount of reagent which becomes bound at two sites is determined and the two values used for an accurate determination of an analyte.

30 Claims, 1 Drawing Sheet

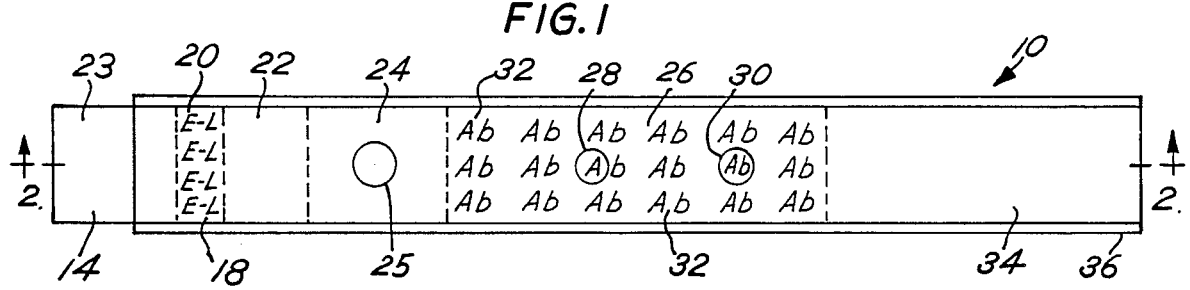
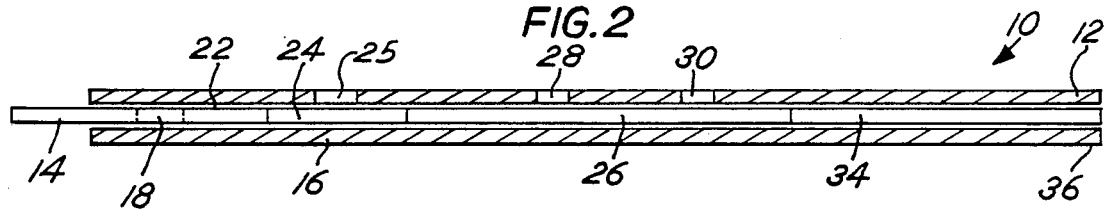
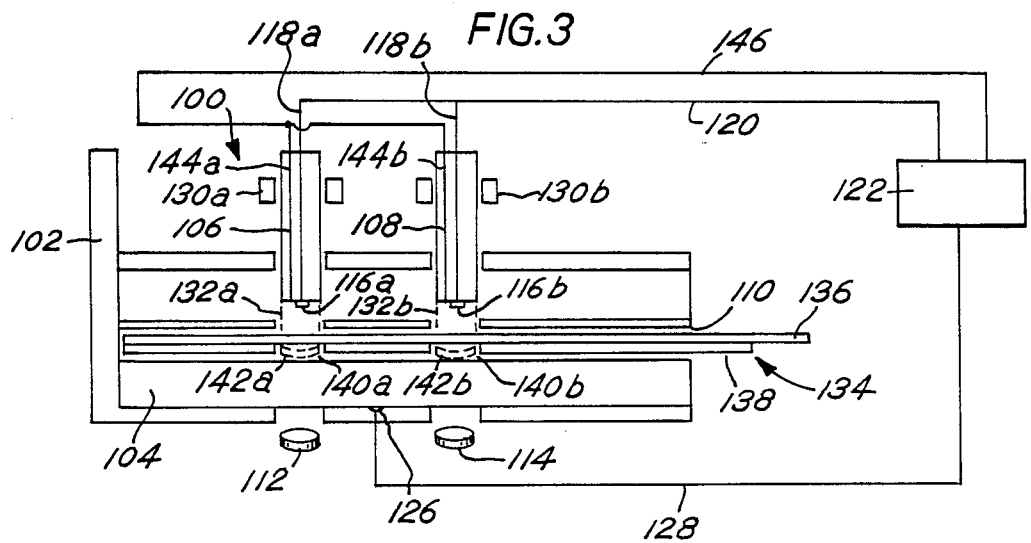
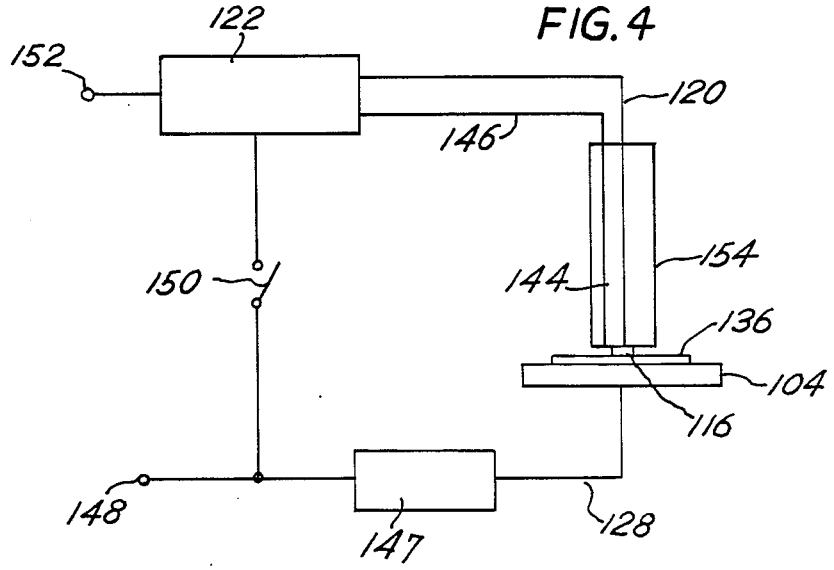

MIGRATORY DETECTION IMMUNOASSAY

TECHNICAL FIELD

The subject invention concerns heterogeneous diagnostic techniques employing a solid bibulous support and specific binding pair members, where the signal generated is related to the amount of analyte in a sample.

BACKGROUND ART

There has been an extraordinary expansion in the interest in being able to measure a wide variety of analytes. This interest has been not only in the field of medicine, but also in other fields, such as processing, molecular biology, ecology and the like. The field of diagnostics has seen the evolution of techniques in whole or in part in solution, involving separation steps or eschewing separation steps, where each of the methods have evolved to provide techniques allowing for detection of analytes at ng/ml levels. However, the solution techniques involve, for the most part, careful measurements, sophisticated instrumentation, and technical sophistication. These techniques have therefore found their primary use in laboratories, which have the available equipment and expertise to perform the assays.

In conjunction with the development of the solution assays, there has been an extensive effort to produce assays involving devices which do not require technical skill. These devices have been primarily directed to the use of sticks or capillaries where the device is contacted with the sample and most of the chemistry is carried out on the device. Usually, the technique requires relatively simple measurements of the sample and/or reagents, and the result can be read either visually or by relatively simple instrumentation. For the most part, these results do not involve a need for accurate quantitative determinations where the amount of analyte is present at extraordinary low concentrations.

Nevertheless, there is an increasing need in hospitals, doctors' offices and in the home to be able to detect a wide variety of analytes which are present at low concentrations, where an accurate determination is necessary for the information to be useful. There still remains a need to provide techniques with simple protocols which can be measured by relatively unsophisticated instrumentation.

RELEVANT LITERATURE

U. S. Patents of interest include U.S. Pat. Nos. 4,168,146, which concerns a test strip for immunoassays, where the extent to which an analyte travels is related to the amount of analyte in the medium; U.S. Pta. No. 4,298,688, which involves a three-zone strip, where the extent of travel of an enzymatic product is determinative of the amount of glucose analyte; U.S. Pat. No. 4,299,916, which concerns an assay technique employing a support for detection of the analyte; U.S. Pat. No. 4,361,537, which employs strips in conjunction with RIAs; U.S. Pat. No. 4,366,241, which concerns employing a small test zone for concentrating a particular component of the assay medium in a small area; U.S. Pat. No. 4,435,504, which concerns an immunochromatograph employing channeling; U.S. Pat. No. 4,442,204, which concerns using homogeneous assay reagents on a solid support where displacement of labeled conjugate-analyte complex by analyte provides the desired signal; U.S. Pat. No. 4,533,629, which employs a simultaneous calibration technique for heterogeneous immunoassays; U.S. Pat. No. 4,446,232, which employs a solid support having a zone occupied by labeled conjugate, followed by receptor, where binding of analyte to the labeled conjugate allows the labeled conjugate to traverse the receptor zone to a detection zone; U.S. Pat. No. 4,447,526, which employs a homogeneous specific binding assay system in conjunction with a carrier matrix; and U.S. Pat. No. 4,454,094, which involves displaced apart layers through which a medium traverses, where reagent from one layer diffuses to the other layer in relation to the amount of analyte in the medium.

SUMMARY OF THE INVENTION

Novel devices and protocols are provided for detecting an analyte in a sample, where the device has at least three zones in the direction of migration of the liquid, (1) the reagent zone, followed by (2) a sample zone, followed by (3) a detection zone, where the sample and detection zones may overlap and optionally a liquid reservoir zone.

In carrying out the assay, a sample is placed in the sample zone and the device introduced into an elution solution whereby the liquid traverses the zones by capillary action, which solution may also include at least one member of a signal producing system. The signal producing system may comprise components which are included in an elution/developing solution and reagents diffusibly bound in the reagent zone, which system results in an extended signal producing area having a signal gradient. By preferably measuring the signal at two or more sites in the detection zone, the relationship between the signals at the various sites can be related to a standard relationship for the determination of the analyte.

BRIEF DESCRIPTION OF THE DRAWINGS

FIG. 1 is a plan diagrammatic view of an assay strip according to this invention;

FIG. 2 is a cross-sectional view along line 2—2 in FIG. 1; and

FIG. 3 is an elevational cross-sectional view of an apparatus for measuring the detectable signal.

DESCRIPTION OF THE SPECIFIC EMBODIMENTS

Devices, protocols and compositions are provided for the detection of an analyte. The device employed is a bibulous strip having at least three zones, where the zones may be designated the reagent zone, the sample zone, and the detection zone, in the direction of migration of liquid across the strip. Two zones may overlap, such as the sample zone and the detection zone.

For the most part, the assays will involve specific binding members or members of an immunological pair ("MIP") where it is understood that the receptors need not be limited to antibodies, but rather, may be any molecule which can be used to distinguish a single or class of molecules from other molecules. That is a MIP is a ligand or receptor which has a specific binding affinity for the other member.

The device is characterized by having in the direction of migration of the eluting solvent, a diffusively bound conjugate comprising a label and a MIP (MIP-label) in the reagent zone. Downstream from the reagent zone will be a zone for application of the sample, the sample zone. Optionally overlapping and either or both upstream and downstream from the sample zone will be a detection zone, which may have one or more reagents bound to the zone, which together with the conjugate in the reagent zone, any reagents in the eluting solvent, and any reagents in a developer comprise a signal-producing system. A fourth zone may be provided which serves to absorb the eluting solvent to insure that the eluting solvent provides at least a minimum volume in excess of the absorbing volume of the other zones, which traverses the first three zones. The detection zone and absorbing zone may also overlap.

The device will be considered first. As already indicated, the device has at least three zones, frequently four zones, where as indicated the sample zone and detection zone may overlap, and the detection zone and absorbing zone may overlap.

The first zone, the reagent zone, will usually be displaced from the eluting solvent receiving end of the strip. A small displacement will suffice to avoid placing the reagent zone with the reagent into the eluting fluid, where reagent may diffuse into the fluid, away from the strip. Usually, a few millimeters will suffice, usually fewer than 10 mm, more usually fewer than about 5 mm, usually at least about 2 mm. The reagent zone will have the conjugate of the label and the MIP, where the labeled MIP may be either a receptor or a ligand. These terms will be defined subsequently.

The reagent zone will generally be at least about 1mm, usually not more than about 1cm, usually not more than about 5mm in the direction of liquid migration. The amount of diffusively bound conjugate in the reagent zone may be varied widely depending upon the manner in which MIP is bound to the bibulous strip, e.g., whether in defined stripes or regions or substantially uniformly over a large area; the sites where measurements are made; the concentration range of the analyte in the sample and the size of the sample, etc. For the most part, the amount of conjugate will be determined empirically. Nevertheless, there will usually be some constraints as to the amount of conjugate.

The amount of conjugate which is present in the reagent zone will normally be sufficient to react with at least about 10% of the MIP present in the detection zone, usually able to provide at least an equivalent number of binding sites as MIP present at the measurement sites in the detection zone up to the furthest upstream measurement site, more usually at least equivalent to the total MIP binding sites, and may be sufficient to saturate the MIP present in the detection zone, or even in substantial excess. That is, for saturation, in the absence of any analyte, the amount of conjugate will be sufficient to bind to all of the available MIP present in the detection zone. Lesser amounts may be employed.

With lesser amounts of conjugate there may be greater sensitivity to inhomogenities and it may be necessary to more carefully calibrate the strip in relation to standard samples having known amounts of analyte, to insure that each batch of strips is uniformly coated with the conjugate and has substantially the same amount of total conjugate at the detection sites. Also, with less than a saturation amount greater care is required in measuring the amount of conjugate which is applied. Therefore, for ease of manufacturing and reproducibility of results, for the most part, the amount of conjugate present in the reagent zone will be a saturating amount, so that there need be only assurance that there is an amount present in excess of a minimum amount.

The sample zone will be a region sufficient to receive a predetermined volume of sample, which will normally be at least about 1 $\mu$l, usually at least about 2 $\mu$l, and usually not more than about 200 $\mu$l, more usually not more than about 100 $\mu$l. While solids or semisolids may be employed as samples, for the most part, liquids are easier to apply and to measure, and to that extent, the sample will be a liquid.

The detection zone will be a zone which will be at least in part coated with a MIP, usually a MIP complementary to or homologous to the MIP of the conjugate, so that the conjugate will bind in the detection zone to those sites of the complementary MIP which are available. As already indicated, there may be a relationship between the amount of reagent in the reagent zone and the amount of MIP in the detection zone.

The bibulous support may be completely coated with MIP in a continuous substantially uniform covering, or only partially coated in a continuous or discontinuous manner. Conveniently, where the bibulous strip is substantially completely covered, it may extend from one end of the strip to the other or only partially to the other end, extending at least through the detection zone. Thus, the reagent zone may include MIP, where the amount of conjugate added will saturate the MIP present in the reagent zone and leave sufficient conjugate for performance of the assay.

The amount of MIP in the detection zone may be related to the amount of analyte which may be found in the sample. The amount of MIP in the sample zone should be capable of binding a substantial portion of the conjugate, up to at least about 50%, usually at least about 100%, so that at the high end of the range of analyte concentration to be encountered, substantially all of the analyte would be bound in the detection zone, conveniently in the sample zone.

The distribution of MIP in the detection zone may be varied widely from substantially homogeneous through a major portion or all of the detection zone, or an increasing or decreasing gradient or a plurality of discontinuous regions which are traversed by the elution solvent front. An increasing MIP concentration gradient in the direction of solvent migration would have the advantage of spreading the binding of the analyte over a larger area at the low end of the concentration range of interest. A decreasing MIP concentration gradient may be useful where the analyte binding affinity and/or conjugate binding affinity varies over a range with a significant proportion of the analyte and/or conjugate having a relatively low binding affinity. Thus, one would ensure that the low binding affinity molecules would be captured within a reasonable area.

An alternative to the use of a complementary MIP would be the use of a receptor which has a much higher affinity for an immune complex than either member of the complex. Such receptors are exemplified by rheumatoid factor or S. aureus protein A. In this situation, the eluent would contain sufficient complementary MIP to react with substantially all the analyte in the sample and the label conjugate. The conjugate containing complex would then be distributed in the reagent zone in relation to the amount of analyte in the sample. While the subject invention may be practiced in this manner, this protocol adds an additional complexity. Therefore, it will usually not be favored, but may find application in certain situations. For the purposes of this invention, the complex may be considered the ligand and the complex binding member the receptor.

The detection zone and sample zone may overlap, where a sample may be placed in the detection zone. In this way, the analyte will bind to MIP present in the detection zone and fill available binding sites. Thus, the reagent conjugate when traversing the sample zone, will fill remaining binding sites and continue past the sample zone into any remaining portion of the detection zone.

Conveniently, a reservoir fourth zone may be provided which will serve to absorb the eluting solvent and may also serve to provide a zone in which a signal may be detected. While for the most part, detection will occur outside the absorption zone, the absorption zone may also serve as a site for measurement, although there will be at least one measurement in the detection zone outside the absorption zone.

For the determination, at least one, usually two or more specific sites are selected for detection of the presence of reagent conjugate. The sites may vary depending upon the nature of the analyte, the nature of the conjugate, the concentration range of the analyte, the sensitivity required for the assay, and the like.

Optionally, a measurement site may be employed between the reagent zone and the sample zone where MIP is distributed through the reagent, sample, and detection zones. Measurement at a site between the reagent zone and the sample zone will provide a saturation standard, that is, the maximum amount of conjugate will be bound. In the absence of analyte, the measurement from this site and the sample site should be substantially the same. Any difference should be related to analyte present in the sample.

The next measurement site will be the sample site, while the farthest detection site will be in the reservoir zone displaced from the end of the strip. There may be one or more sites between these two sites. The choice of location will be affected by the nature of the detectable signal and the manner in which it is generated. Where diffusion of the agent providing the detectable signal occurs with migration of the eluent solvent, a detection site may be downstream from the region where MIP complex formation occurs. Where the agent providing the detectable signal becomes bound at the site of the MIP complex formation, usually the detection site(s) will be selected to substantially optimize the difference in the detectable signal at the two sites over the concentration range of interest. The detection sites will usually be separated sufficiently to minimize interference from adjacent sites, 0.5mm, usually 1mm, or more usually sufficing.

One desirable distribution of sites is where the sample is placed in the detection zone, a saturating amount of reagent is employed, a uniform MIP concentration in the detection zone is employed and the reagent for purposes of measurement is treated as stationary. In this situation two detection sites would suffice, where the second site is beyond the substantial exhaustion of the analyte in the detection zone, so that a substantially constant value is observed at the second site, and the value varies with the amount of analyte at the first site. Another situation would be where both sites are downstream from the sample site and the proportion of analyte at each site will vary with the amount of analyte in the sample. Where instead of a homogeneous MIP field, a decreasing gradient in the downstream direction is employed, measurement sites would be selected empirically which would provide the greatest sensitivity, in giving the largest value spread over the concentration range of interest. Another situation would have a first detection zone as the standard (constant value) located between the reagent zone and the sample zone and the second detection site within the sample zone. The relationship observed between the two sites would be related to analyte, since the conjugate should substantially saturate all binding sites at the first detection site.

The receptor may be any molecule which has a specific binding affinity for another molecule. While antibodies find the most general use, other molecules may serve as receptors, such as enzymes, surface membrane receptors, single stranded nucleic acids, lectins, toxins, or the like. For the most part, the molecules will be proteinacious and may be naturally occurring, obtained by synthesis or recombinant techniques. The ligand may be any molecule for which a receptor exists or may be prepared. For the most part, ligands will be organic molecules of at least about 125 daltons (D), and may be 1000 kD or more, usually below about 1000 kD. The ligands may be individual molecules or parts of aggregations, such as membranes, capsids, cells, etc.

The bibulous support may be a single material or a variety of materials, which allow for capillary transport of a liquid. Various filter materials or membrane materials may be employed for the different zones or a single material may be employed. Included among materials which may find use are polysaccharides, e.g., cellulose materials, such as paper, cellulose acetate, nitrocellulose; and organic materials, such as silica, deactivated alumina, diatomaceous earth, magnesium sulfate, glass fibers or other inorganic finely divided material conveniently substantially uniformly dispersed in a porous polymer matrix, with polymers such as vinyl chloride, vinyl chloride-propylene copolymer, vinyl chloride-vinyl acetate co-polymer; cloth, both naturally occurring, e.g., cotton and synthetic, e.g., nylon cloth; etc.

The significant factor is that the various materials support capillary action, do not interfere with the movement of diffusible materials, allow for covalent binding, as appropriate, and do not interfere with the production and detection of the signal. Support materials will be selected in relation to the stability of the reagents bound to the support, the way in which the fluid traverses the support, the nature of the signal, or the like.

The device may have a supporting layer which may be of any convenient material, which is various inert plastics, such as polyvinylchloride, polystyrene, polyacrylamide, etc. where the support will give mechanical stability to the bibulous layer. Conveniently, the support can serve to identify the various zones, by allowing for an opening or positioning the sample and having additional openings for the sites for detection. In addition there may be an additional supportive layer so as to form a sandwich, where the additional layer may or may not have the same openings as the other support layer. Alternatively, the support may be one or two supporting rods along the edge or other convenient configuration.

While the dimensions of the test strip may vary widely, the length will normally be substantially greater than the width, usually at least two times greater than the width, and may be ten times or more greater than the width. The width and thickness may be regular or irregular, depending upon the nature of the various materials and zones. Generally, the device will be at least about 1mm wide, and usually not more than about 10mm wide, generally being at least about 1cm long, and usually not more than about 5cm long. These values are not critical, but rather are convenient for the nature of the assay and the manner in which the assay is performed.

The reagent zone may be 1mm or more across the strip, depending upon the concentration of the reagent and the amount required. Usually, the reagent zone will not extend to greater than about 5mm. The sample zone will have a dimension in the direction of migration in the range of about 1 to 5mm. The detection zone will usually be at least 5mm and may be 1cm or more, while the absorption zone can be any convenient size, depending upon the amounts of liquid to be absorbed and the nature of the absorbent material. For convenience, it will usually be not greater than about 2cm.

In impregnating the detection zone, various concentrations of MIP may be employed, generally providing about $10^{-5}$ to $10^{-14}$ mol/cm$^2$, more usually from about $10^{-7}$ to $10^{-12}$ mol/cm$^2$. Depending upon the nature of the MIP, various methods may be employed for nondiffusibly binding the MIP to the surface. Where proteins are involved, with many supports, heat will suffice to insure the substantial immobility of the protein. Alternatively, the surface may be functionalized with a wide variety of functionalities such as cyanogen bromide, diazobenzyloxy groups, halomethyl groups, succinic acid, glutaraldehyde, maleimidobenzoic acid, etc. Where the MIP is non-proteinaceous, frequently the MIP will be modified to provide for a functional group which can be covalently bonded to the bibulous support.

A wide variety of analytes may be determined, varying from simple inorganic or organic molecules or ions to large complicated assemblages of molecules, such as viruses, cells, cell components or fragments, e.g., cell membranes, etc. U.S. Pat. No. 4,366,241 has a list of analytes bridging columns 19 to 26, which disclosure is incorporated herein by reference.

The MIP-label will be diffusibly positioned in the reagent zone. Therefore, the material employed as the bibulous support will be one to which the conjugate will not become immobilized. Conveniently, a solution of the conjugate may be spotted, sprayed, or otherwise applied to the reagent zone and the solution evaporated, resulting in deposit of the conjugate in the reagent zone. By appropriate choice of concentration of the conjugate in the solution, the desired amount of conjugate may become bound in the reagent zone. The amount of reagent conjugate applied to the reagent zone will generally be in the range of 10 pg to 100 ng. Other materials may also be included in the solution of the reagent conjugate, such as buffers, stabilizers, other reactants, biocides, salts, etc.

The assay method employed may vary with the nature of the analyte, the particular format of the device, the signal producing system, and the method for detection.

The signal producing system will comprise at least the reagent conjugate. With enzymes, the signal producing system will require at least one substrate, but may also include other substrates, cofactors, one or more additional enzymes and their substrates and cofactors, and the like. Except for the reagent conjugate, the other members of the signal producing system may be distributed among the eluting solvent, the bibulous support, particularly the detection zone, an independent developer solution with which all or a part of the detection zone may be contacted, for example, by immersion, spraying, addition, capillary migration or the like.

For the most part, the signal producing system will involve an enzyme as a label, where the enzyme is conjugated to a MIP. The other members of the signal producing system may include a second enzyme, where the product of the first enzyme is the substrate of the second enzyme. The enzymatic product may be any substance which provides a detectable signal, such as light absorption or emission, change in pH, change in redox potential, or the like. By light absorption is intended absorption of light, which may be in the ultraviolet or the visual range, radiation having a wavelength in the range of about 350 to 800 nm. Alternatively, the enzyme may provide for a change in pH, or a change in the redox potential of the medium. Various devices are available for detection of changes in pH, or changes in redox potential, such as U.S. application Ser. No. 876,925, PCT/U585/00336, EPO 85.104846.2 and EPO 86.306176.8, whose disclosures are incorporated herein by reference.

The technique referred to as channeling can be employed, where two enzymes are employed, one of the enzymes being bound in the detection zone, and the other enzyme being the label of the MIP-label conjugate. In this situation, the product of one enzyme is the substrate of the other, with the result that a product is produced which provides for a detectable signal. In this situation, the eluting solvent may employ the substrate of the enzyme bound to the support in the detection zone, as well as all other necessary components of the signal producing system, where reaction will only occur to produce the product providing the detectable signal, where the enzyme conjugate is bound in the detection zone.

A large number of enzymes and co-enzymes for providing products which provide a detectable signal may be found in U.S. Pat. No. 4,275,149, bridging columns 19-23, and U.S. Pat. No. 4,318,8980, bridging columns 10-14, which disclosures are incorporated herein by reference. A number of enzyme combinations are set forth in U.S. Pat. No. 4,275,149, bridging columns 23-28, which disclosure is incorporated herein by reference.

Of particular interest are oxidoreductase enzymes which involve the production of hydrogen peroxide and the use of hydrogen peroxide to oxidize a dye precursor to a dye, or change the redox potential of an assay medium. Particular combinations include saccharide oxidases, e.g., glucose and galactose oxidase, or heterocyclic oxidases, such as uricase and xanthine oxidase. For producing a colored product, these enzymes may be coupled with an enzyme which employs hydrogen peroxide to oxidize a dye precursor, e.g., peroxidase, microperoxidase and cytochrome oxidase. Additional enzyme combinations may be found in the subject matter incorporated by reference.

Another group of enzymes of interest are oxidoreductases involving AND(H) or NADP(H) which can be coupled to redox systems, e.g., inorganic metal couples such as ferro- and ferricyanide, for detection. Enzymes which find use include malate dehydrogenase, urease, glucose-6-phosphate dehydrogenase, lactate dehydrogenase, 3-hydroxybutyrate dehydrogenase, alcohol dehydrogenase, glyceraldehyde-3-phosphate dehydrogenase, etc.

Another group of enzymes of interest are hydrolases and transferases resulting in the formation or loss of an acidic or basic species, which results in a change in pH. Illustrative enzymes include alkaline phosphatase, sulfatases, acid phosphatase, saccharidases, e.g., β-galactosidase and β-glucosidase, pyrophosphatase, carboxylic ester hydrolase, peptidases, etc. These enzymes may also find use in producing colored products, for example, hydrolysis of umbelliferyl phosphate or the di-β-galactosidyl ether of fluorescein.

Other enzymes may also find use, such as lyases, isomerases, ligases, or synthetases.

Illustrative co-enzymes which may find use include AND[H], NADP[H], pyridoxal phosphate; FAD[H]; FNM[H]; etc. usually co-enzymes which combine with oxidoreductases.

In carrying out the method, the sample is placed in the sample zone, where the sample may have been subject to prior treatment, depending on the nature of the sample. In the case of blood, whole blood may be used, serum or plasma. In other media, particulate matter may be removed, such as cells, particles or the like. The sample may have been subjected to heat, filtration, chromatography, electrophoresis or other treatment, where interfering materials may be removed, the desired material concentrated, buffers added, etc.

Conveniently, the sample zone may be used for filtration. The sample may be directed by a cone or cylinder to the sample zone and drawn through the sample zone by any convenient means, e.g. pressure differential, absorbent, etc. In this manner, the analyte may be concentrated in the sample zone.

After the sample has been placed in the sample zone, the device is then partially immersed, usually a few millimeters of the end closest to the reagent zone being dipped into the eluent solution. The eluent solution may be a buffered aqueous solution, generally buffered at a pH in the range of about 5.5 to 10, more usually in the range of about 6 to 9.

Various buffers may be used, usually buffers which will be appropriate for complex formation, and, as appropriate, the signal producing system. Illustrative buffers include phosphate, borate, tris, MOPS, carbonate, etc. Normally, the concentration of the buffer will range from about 0.1 to 500 mM.

Besides buffer, other solutes may be present, as already indicated, as components of the signal producing system. The components of the signal-producing system may be present when kinetic determinations are made or when a channeling reaction is involved and will usually be absent where an endpoint determination is involved.

The eluent is allowed to migrate up the strip until the leading edge of the eluent has reached a predetermined site, conveniently, the end of the strip. The device may then be removed from the eluent. Where the eluent contains the components of the signal producing system, the device will be measured at the sample site or at two or more measurement sites, usually within a fixed period of time. Where the eluent does not contain the remaining members of the signal producing system, the device will be introduced into a developer solution, containing the remaining components and the reaction allowed to proceed for a predetermined period of time. The device may then be removed from the developer solution, and, depending upon the nature of the signal, may be washed or measured directly.

Measurements will be made at one or more sites, separated by at least about 1mm, and usually not more than about 5cm, more usually not more than about 2cm.

At each site there will be a signal as a result of the presence of MIP-label so that factors affecting the signal unrelated to the amount of analyte will affect the observed signal at each site. The measurement may be light absorption, light emission, voltage, current, or the like, where the change in electrical signal may be as a result of a change in electromagnetic characteristics of the solution, pH, or redox potential. The mathematical relationship between the readings at the various sites provides a value (e.g. difference, ratio slope, etc.), which is related to the analyte. By employing standards having known amounts of analyte, the value which is determined can be related to the value obtained with the standard, determined under substantially the same conditions, so as to provide a quantitative result for the determination.

As a matter of convenience, the device can be provided in combination with other reagents for use in assaying for an analyte. Where two enzymes are involved, the other reagents will include enzyme-labeled MIP, substrate for the enzyme bound to the support, any additional substrates and co-factors required by the enzymes, and where light absorption, reflectance or emission is involved, the dye precursor, which provides the detectable chromophore, chemiluminescer or fluorophore. As appropriate, where a single enzyme is employed, the appropriate substrate may be provided in conjunction with the device. In addition, other additives may be included, such as stabilizers, buffers, and the like.

The relative amounts of the various reagents may be varied widely to provide for concentrations in solution of the reagent which substantially optimize the sensitivity of the assay. Particularly, the reagents may be provided as dry powders, usually lyophylized, including excipients, which on dissolution will provide for a reagent solution having the appropriate concentrations for combining with the sample.

For further understanding of the subject invention, the drawings will now be considered.

Various protocols and formats may be employed in carrying out the assay. One illustrative format employs a visual signal which can be determined by comparison with a color standard or by spectrophotometric analysis. In this protocol the conjugate is haptenurease conjugate. The device has an excess of the conjugate over the antibody present in the detection zone. The antihapten in the detection zone is uniformly distributed. The bibulous support has an inert plastic support with three openings (ports) for detection sites. Two of the openings are side-by-side, one to receive sample and the other to act as a comparison and displaced from the sample port a sufficient distance to preclude any significant amount of analyte in the sample from diffusing over to the control region. The sample and control ports overlap the detection zone.

In this configuration, the bibulous support is uniformly coated with MIP (anti-hapten antibody). The assay is carried out as follows. A measured amount of sample is placed on the bibulous support through the sample port. An equal volume of buffer or other fluid containing a known amount of analyte, including no analyte, is placed on the support through the adjacent port. The device is used directly or allowed to incubate for a short time, e.g., 0.5 min. or longer, for complex formation to occur. The device is then immersed at one end in the eluent, a phosphate buffered saline solution (PBS), pH6, having about 1 mg/ml of a non-specific protein to bind non-specifically to the bibulous support and dilute the hapten-urease conjugate. A small amount of a non-ionic detergent may also, be included, such as 0.01% Tween 20—brand of polyoxyethylenesorbitan monolaurate nonionic detergent—or Triton X-100— brand of octylphenoxypolyethoxyethanol nonionic detergent.

The device is maintained with the end immersed in the eluent until the front has passed through the absorption zone to the end of the bibulous strip. The device is removed from the eluent and immersed in a developer solution comprising PBS (1mM $PO_4$, 150 mM NaCl), 100 mM urease and 450 $\mu$M cresol red. If horse radish peroxidase was used as the enzyme the developer would be a 1:1 mixture of Kirkegaard and Perry Labs, Reagents A & B (lab #50-62.00, 2.2'-azino-di-(3 ethylbenzthiazolinyl-6-sulphonic acid as the dye) or one or more drops of the developer solution could be placed on the bibulous support, where the developer solutions provides a large excess of the substrate. In this way, the rate of the enzymatic reaction remains substantially constant during the course of the assay. The light absorption would be determined at the sample site; the control site, which may be upstream or downstream from the sample site; and optionally, an additional measurement site downstream from the sample site. By using color standards, the quantity of the product of the enzymatic reaction at each of the sites could be designated with a numerical value, where a relationship between the sample site and upstream measurement site would provide a semi-quantitative value for analyte. The relationship between the measurement site and control site would serve as a control to ensure nothing untoward had occurred.

Another protocol would involve a similar system to the system described above except that a hydrophobic leuco dye would be distributed uniformly in the detection zone which would be limited to the sample region and a region upstream from the sample zone. The conjugate would be antigen-horse radish peroxidase and the eluent would be dilute hydrogen peroxide. As the eluent migrated through the bibulous support there would be no reaction until the front entered the detection zone. Upon the front encountering the sample zone, a proportion of the anti-antigen binding sites unfilled with antigen would be filled by the antigen conjugate. Once the front passes the sample zone, the appropriate proportion of anti-antigen sites would be filled in accordance with the concentration of antigen conjugate and the binding affinity of the anti-antigen. Thus, the binding of conjugate at the sample site and the measurement site will differ in proportion to the amount of analyte. The device may be introduced into a reflectometer and the rate of change of absorption determined. By relating the rate at the measurement site to the rate at the sample site, the resulting value may be related to a standard for quantitation.

In FIGS. 1 and 2, is depicted a device 10 having upper layer 12 of an inert material acting as a cover and holder for bibulous strip 14, which is optionally supported by inert film 16. The bibulous strip 14 has a plurality of zones comprising a first zone 22 which includes the reagent zone 18. The reagent zone has the reagent, enzyme-MIP conjugate, which is indicated as E-L 20, representing enzyme-ligand. The first zone 22 extends beyond layer 12 to provide an exposed absorbent zone 23 for immersion in the eluent. Zone 22 may be any convenient material which provides for convenient absorption of the eluent, diffusive binding of the enzyme-ligand 20, and storage stability of the enzyme-ligand. Thus, zone 22 may be the same or different material from the other zones. The second zone 24 includes the sample receiving site, where upper layer 12 has opening 25 for introducing the sample to be bound to zone 24. Zone 24 may be the same or different material from the material employed for zone 22. In addition, reagents may be impregnated in zone 24 to interact with the sample to provide for desired properties associated with the analyte.

Detection zone 26, which could include sample zone 24, has two viewing ports, 28 and 30, defining measurement sites. Bound to zone 26, in this particular mode are antibodies indicated as Ab 32, although the antibodies could be uniformly distributed over the entire bibulous support 14. This zone may be of the same or different material from the other zones, depending upon the particular assay and the nature of the reagents involved. Desirably, the detection zone 26 will be prepared of a material which allows for stability and retention of activity of the MIP bound to the surface. The next zone, which is optional, will be the absorption zone 34, which will serve as a reservoir to receive the eluent and may in some instances also serve as an extension of the detection zone, where a determination of the signal may be made in this zone at a detection site, not indicated.

In carrying out the assay, the sample would be introduced onto the bibulous support 14 at sample zone 24 through port 25. The device 10 would then be introduced into an eluent where the zone 23 would be immersed in the eluent. After sufficient time for the eluent to traverse the strip and reach the end 36, the device would be removed from the eluent and, depending on the protocol measured or could be then completely immersed in a developer solution, where the enzyme would react with the substrate through ports 25, 28 and 30. Measurements could be made, not only at sites 28 and 30, but also at zone 22, downstream from the reagent zone 18, at sample zone 24, or any combination thereof.

In FIG. 3 is depicted a sensor apparatus which is described in more detail in application Ser. No. 876,925, filed June 20, 1986, whose disclosure is incorporated herein by reference. The apparatus 100 comprises a housing 102, a photosensitive pH sensitive semiconductor 104, two pistons 106 and 108, a device receiving compartment 110 and light sources 112 and 114. The pistons have counter electrodes 116a and 116b connected through leads 118a and 118b and common lead 120 to potentiostat 122. Semiconductor or working electrode 104 is connected to potentiostat 122 by means of ohmic contact 126 and lead 128. The pistons 106 and 108 are actuated by means of coils 130a and 130b, respectively. The pistons 106 and 108 are directed downwardly to positions 132a and 132b, respectively, as indicated by the broken lines.

In carrying out the determination, the device 134 is inserted into substrate containing device receiving compartment 110 to abut against housing 102. The device 134 has bibulous strip 136 and inert support 138. Inert support 138 has first detection site opening 140a and second detection site opening 140b. After inserting the device 134 into the compartment 110, the coils 130a and 130b are actuated to drive the pistons 106 and 108 against the bibulous strip 136 through the detection site openings 140 and against working electrode 104. The bibulous strip will then be between the counter electrodes 116a and 116b and the working electrode 104 as indicated by the broken lines 142a and 142b, to complete the circuit at the detection site openings 140a and 140b, respectively. As appropriate, reference electrodes 144a and 144b may be provided to ensure a standard for the circuitry. The reference electrodes 144a and 144b extend beyond the bottom of pistons 106 and 108, respectively, so as to contact the bibulous strip 136 with counter electrodes 116a and 116b, respectively. The reference electrodes 144a and 144b are connected to potentiostat 122 through common lead 146.

Light sources 112 and 114 will then be used to sequentially irradiate working electrode 104 in relation to detection site openings 140a and 140b. Depending upon the protocol employed with device 134, members of a signal producing system will be present on the bibulous strip, which will result in a signal detectable by the working electrode. The signals at the two sites will be different in relation to the amount of analyte in a sample which is placed at site 140a on the bibulous strip. The relationship of the signal obtained at site 140a as compared to 140b will provide a quantitative value for the analyte.

One suitable circuit for the measurement of the photoresponse or other electrical signal generated with the electrochemical cells of apparatus 100 involves automatically varying the potential between counter electrodes 116a and 116b and working electrode 104 so as to maintain a constant amplitude sinusoidal current through counter electrodes 116a and 116b in response to sinusoidal irradiation with light sources 112 and 114 on working electrode 104 in relation to detection site openings 140a and 140b. Thus, variation in the chemical environment near working electrode 104 can be determined by measuring the potential required to maintain a constant current. This measurement scheme is referred to as the constant amplitude mode.

A second suitable circuit for the measurement of the photoresponse or other electrical signal generated with the electrochemical cell of apparatus 100 involves sweeping the potential between counter electrodes 116a and 116b and working electrode 104 and measuring the amplitude of the alternating current through the circuit, where the current is induced by sinusoidal irradiation of the working electrode 104. The array thus produced, applied potential vs. photocurrent amplitude, is analyzed with digital electronics to determine the applied potential which corresponds to the point of maximum slope on the plot of photocurrent amplitude vs. applied potential. This potential is dependent in a quantitative manner on variations in the chemical environment at openings 140a and 140b. This measurement scheme is referred to as the constant potential mode.

A block diagram of an exemplary circuit is shown schematically in FIG. 4, which shows silicon working electrode 104, counter electrode 116, and reference electrode 144, and electrochemical cell container 154. Potentiostat 122 controls the potential between bibulous support 136 and working electrode 104 by monitoring the potential of the medium in the bibulous support 136 through reference electrode 144 and applying the necessary potential to counter electrode 116. Alternating current ammeter 147 measures the alternating current through working electrode 104 and outputs a potential proportional to the amplitude of this current to output 148. This signal is used in the constant potential mode. In this mode switch 150 would be open. When switch 150 is closed a feedback loop to potentiostat 122 is formed which allows potentiostat 122 to maintain a potential from the medium to working electrode 104 such that a constant photoinduced AC current is maintained through working electrode 104. In this constant amplitude mode, potentiostat 122 at output 152 provides a voltage proportional to the potential from the medium in the bibulous support 136 to working electrode 104.

EXPERIMENTAL

The following examples are offered by way of illustration and not by way of limitation.

A device was prepared using 12 $\mu$ Schleicher and Schuell nitrocellulose, or 5 $\mu$ Millipore Immobilon—brand of polyvinyldifluoride base membrane coated with carbonyldiimidazole-reacted hydroxylate—as the detection zone substrate. An antibody solution was prepared containing a predetermined amount of rabbit anti-digoxin bulked to 1 mg/L with rabbit immunoglobulin. The antibody solution medium was 0.1% glutaraldehyde in phosphate-buffered saline (PBS); 0.035M disodium acid phosphate, 0.015 M sodium diacid phosphate; 150 mM NaCl. Other reagents employed were 0.2% polyvinyl alcohol (PVA), and 0.1 M ethanolamine, pH 9.5.

For functionalizing the nitrocellulose, the nitrocellulose membrane was dipped into the antibody solution, incubated for 45 min., followed by the addition of 500 $\mu$l of PBS, the mixture allowed to stand for 15 min, followed by decanting the liquid. To the membrane was then added 500 $\mu$l of the glutaraldehyde solution, the reaction allowed to proceed for 16 min, followed by decanting of the reaction mixture, washing the strip 2× with PBS, 1× with deionized water, where each washing was performed for 15 min. To the strip was then added the PVA solution, the mixture incubated for 15 min, followed by blotting and drying for 15 min.

For the Immobilon layer, the membrane was introduced into the antibody solution and incubated for 45 min. To the solution was then added 500 $\mu$l of ethanolamine, followed by incubating overnight and then decanting. The strip was then washed 2× in PBS, 1× in deionized water, each washing for 15 min. The PVA solution was then added and the mixture incubated for 15 min, followed by blotting and drying for 15 min.

The urease-digoxigenin conjugate was prepared by first combining as dry powders 3-dehydrodigoxigenin-3-0-carboxymethyloxime (CMOD; Molecular Probes); 1.4 mg 1-ethyl-3-(3'-dimethylaminopropyl) carbodiimide (EDAC; BioRad) and 0.33 mg N-hydroxy succinimide (NHS; Sigma), the powdered mixture dried under vacuum at 37° C. overnight, followed by the addition of 1 ml dimethylformamide and the reaction mixture allowed to stand overnight at room temperature. Various mole ratios of CMOD to urease were prepared by adding different volume amounts of the CMOD solution to aliquots of urease (2 ml, 1 mg urease/ml in 0.1 M sodium carbonate, pH 9.0). The reaction mixture was allowed to stand overnight, followed by dialysis vs PBS, pH 7.0 at 4° C. overnight, with 3 buffer changes.

The device which was employed was a laminated stick 9×70mm. Each of the membranes were laminated to plastic with double stick adhesive. The conjugate was applied to a glass fiber membrane, Whatman, GF/C, untreated, 30mm long, by spotting 5 $\mu$l of the urease conjugate at a concentration of 5 $\mu$g/ml downstream from the membrane end. Downstream from the conjugate was spotted 5 $\mu$l of sample, where the sample was placed near one end of a 25mm strip of antidigoxin functionalized nitrocellulose, prepared as described above. Next was the absorption reservoir zone which was Whatman 31 ET, untreated, 15mm long. The assay was carried out by immersing the bottom of the strip, approximately 5mm in the eluent and allowing the eluent to migrate to the top of the strip, which required about 4 min. The eluent formulation was 10 mM $NaPO_4$, 0.15 M NaCl, 1 mg/ml BSA pH 6.0. Substrate solution in the sensor was 100 mM urea, 150 mM NaCl, 40 mM EDTA, pH 6.0. The strip was then introduced into the sensor, described in U.S. Application Ser. No. 876,925, and the rate of change in pH as a result of hydrolysis of the urea determined. The following table indicates the results.

TABLE 1

| Dig (ng/ml) | $A_1$ (top) $\mu V/S$* | $A_2$ (bot.) $\mu V/S$* | Top/Bot | |
|---|---|---|---|---|
| 0 | 171 | 241 | 0.71 | |
|  | 201 | 255 | 0.79 | $x = 0.79 \pm 0.085$ |
|  | 183 | 214 | 0.88 | |
| x | $187 \pm 15.0$ | $237 \pm 20.8$ | 0.79 | |
| 2 | 188 | 174 | 1.08 | |
|  | 167 | 173 | 0.97 | $x = 1.06 \pm 0.247$ |
|  | 138 | 174 | 0.79 | |
|  | 227 | 164 | 1.38 | |
| x | $180 \pm 37.4$ | $171 \pm 4.8$ | 1.05 | |
| 5 | 192 | 85 | 2.26 | |
|  | 251 | 115 | 2.18 | $x = 2.03 \pm 0.326$ |
|  | 159 | 96 | 1.66 | |
| x | $201 \pm 46.6$ | $98.7 \pm 15.1$ | 2.04 | |
| 10 | 193 | 67 | 2.88 | |
|  | 199 | 66 | 3.01 | $x = 3.06 \pm 0.204$ |
|  | 174 | 53 | 3.28 | |
| x | $189 \pm 13.1$ | $62 \pm 7.8$ | 3.05 | |

*$\mu V/S$ = microvolts/sec

It is evident from the above results, that accurate assays can be obtained from a wide variety of analytes using the subject techniques by employing two sites, rather than a single site for determination. Thus, errors resulting from the system unrelated to the analyte amount can be subtracted or reduced so as to greatly enhance the sensitivity of the assay. In this manner, a rapid and simple technique is employed using a device which can be readily manipulated and used by unsophisticated individuals. Also, in combination with various sensors which are commercially available or can be adapted to the present device, the results can be determined in a rapid automated manner.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of an analyte in a sample suspected of containing said analyte, said method employing a strip device capable of providing capillary transport and comprising at least four regions: in the direction of eluent migration (1) a reagent region displaced from a first end of said strip device, containing a reagent consisting of a labeled specific binding member diffusibly bound to said strip, (2) a first detection region comprising a bound complementary specific binding member of said labeled specific binding member, said complementary specific binding member being capable of specifically binding (3) a sample region for receiving said sample; and (4) a second detection region comprising the bound complementary specific binding member of said labeled specific binding member wherein said second detection region nay extend from said reagent region into any reservoir region; with the proviso that said sample region and said second detection region may overlap, said method employing a signal producing system capable of producing a detectable signal at said second detection region and comprising said labeled specific binding member; said method comprising adding said sample to said sample region;

immersing said first end in an eluent to provide a moving liquid phase through said strip, whereby said eluent migrates through said strip carrying said labeled specific binding member and, when sample is outside said detection region, carrying sample into said detection region, and distributing said labeled specific binding member within at least one measurement site in said second detection region in relation to the amount of analyte in said sample, wherein there are at least two spatially separated measurement sites; and determining the amount of bound labeled specific binding member by means of said signal producing system at said measurement sites as compared to a sample having a known amount of analyte, where the relationship between the amounts at the different sites is compared to the relationship obtained with a sample having a known amount of analyte.

2. A method according to claim 1, wherein said labeled specific binding member comprises an enzyme label.

3. A method according to claim 2, wherein said enzyme is an oxidoreductase.

4. A method according to claim 2, wherein a single determination is made at the sample region.

5. A method according to claim 1, wherein said complementary specific binding member is an antibody.

6. A method according to claim 5, wherein said antibody is uniformly distributed in said detection region.

7. A method according to claim 5, wherein one of said measurement sites is said sample region, where said sample region overlaps said detection region.

8. A method according to claim 1, wherein said labeled specific binding member is present in said reagent region in sufficient amount to substantially saturate the complementary specific binding member in said detection region in the presence of analyte in the sample at the maximum amount of the range of interest of said analyte.

9. A method according to claim 1, wherein said labeled specific binding member comprises an enzyme label and said eluent comprises at least one member of said signal producing system.

10. A method according to claim 9, wherein said one member of said signal producing system is a substrate or cofactor—for said enzyme.

11. A method according to claim 1, including the additional step of contacting said measurement sites with a developer solution containing additional members of said signal producing system.

12. A method according to claim 1, wherein said strip device is comprised of a plurality of bibulous materials.

13. A method according to claim 1, wherein said specific binding member is distributed uniformly through said detection region.

14. A method according to claim 1, wherein said specific binding member is distributed non-uniformly through said detection region.

15. A method for determining the presence of an analyte in a sample suspected of containing said analyte, said method employing a strip device capable of providing capillary transport and comprising a bibulous layer with a least four regions: in the direction of eluent migration (1) a reagent region displaced from a first end of said strip device, containing a reagent consisting of an enzyme labeled specific binding member diffusibly bound to said layer, (2) a first detection region comprising the bound complementary specific binding member of said enzyme labeled specific binding member, said complementary specific binding member being capable of specifically binding said analyte, (3) a sample region for receiving said sample; and (4) a second detection region comprising the bound complementary specific binding member of said enzyme labeled specific binding member; with the proviso that said sample region and said second detection region may overlap, and an inert support layer overlapping said bibulous layer and providing for access to said first end and at least two detection sites in the second detection region; said method employing a signal producing system capable of producing a detectable signal at said detection sites and comprising said enzyme labeled specific binding member and enzyme substrate; said method comprising:

adding said sample to said sample region;

immersing said first end in an eluent to provide a moving liquid phase through said strip, whereby said eluent migrates through said strip carrying said enzyme labeled specific binding member and, when sample is outside said second detection region, carrying sample into said second detection region, and distributing said enzyme labeled specific binding member through said second detection region in relation to the amount of analyte in said sample; and determining the amount of bound labeled specific binding member by means of said signal producing system at least two spatially separated detection sites, where the relationship between the amounts at the different sites is compared to the relationship obtained with a sample having known amount of analyte.

16. A method according to claim 15, including the additional step of contacting said detection sites with a developer solution comprising additional members of said signal producing system to produce a signal resulting in light absorption.

17. A method according to claim 15, wherein one of said detection sites is the sample region.

18. A method according to claim 15, wherein one of said detection sites is between said reagent region and said sample region.

19. A method according to claim 15, including the additional step of contacting said detection sites with a developer solution comprising additional members of said signal producing system to produce a signal resulting in a change in pH.

20. A method according to claim 15, including the additional step of contacting said detection sites with a developer solution comprising additional members of said signal producing system to produce a signal resulting in a change in redox potential.

21. A method according to claim 15, wherein said eluent comprises additional members of the signal producing system.

22. A strip device capable of providing capillary transport and comprising a bibulous layer comprising at least four regions: in the direction of eluent migration (1) a reagent region displaced from a first end of said strip device, containing a reagent consisting of a labeled specific binding member diffusibly bound to said strip wherein said labeled specific binding member is member of a signal producing system; (2) a first detection region comprising the bound complementary specific binding member of said labeled specific binding member, said complementary specific binding member being capable of specifically binding an analyte; (3) a sample region for receiving said sample; and (4) a second detection region comprising the bound complementary specific binding member of said labeled specific binding member; with the proviso that said sample region may overlap with any detection region, but each detection region must be spatially separated from every other detection region, and an inert support layer overlapping said bibulous layer and providing for access to said first end and said detection sites.

23. A strip device according to claim 22, wherein at least two of said regions are of different materials.

24. A strip device according to claim 22, wherein said bound complementary specific binding member is substantially uniformly distributed through said sample region and said first and second detection regions.

25. A strip device according to claim 22, wherein said labeled specific binding member comprises an enzyme label.

26. A strip device according to claim 22, wherein said sample region overlaps said first and second detection regions, and said sample region is one of said detection sites.

27. A strip device according to claim 22, wherein said first and second detection regions comprise members of said signal producing system.

28. A kit comprising a strip device according to claim 25, substrate for said enzyme and any required cofactors for said enzyme.

29. A method according to claim 1 or 5, further comprising a reservoir region with a second end, wherein said second detection region and said reservoir region may partially overlap.

30. A strip device according to claim 22, further comprising a reservoir region, wherein said second detection region and said reservoir region may partially overlap.

* * * * *